US00PP09744P

United States Patent [19]

Dümmen

[11] Patent Number: Plant 9,744

[45] Date of Patent: Dec. 10, 1996

[54] GERANIUM PLANT NAMED 'HWD AIDA'

[75] Inventor: Günter Dümmen, Rheinberg-Eversael, Germany

[73] Assignee: Dummen Jungpflanzenkulturen, Rheinberg-Eversael, Germany

[21] Appl. No.: 517,834

[22] Filed: Aug. 22, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of geranium plant named HWD Aida, characterized by its semi-double dark red flowers; compact to medium plant size; distinctly zoned foliage; and basal branching plant habit.

1 Drawing Sheet

The present invention relates to a new and distinct cultivar of geranium plant, botanically known as *Pelargonium×hortorum*, known as the variety Dueaida, and hereafter referred to by the cultivar name HWD Aida.

The new cultivar is a product of a planned breeding program conducted by the inventor in Rheinberg, Germany. The objective of the breeding program was to develop a new dark red, semi-double-flowered variety with zoned foliage.

The new cultivar originated from a cross made by the inventor of the proprietary selection 85-10-2 as the male or pollen parent with the proprietary selection 85-4-4 as the female or seed parent.

The cultivar HWD Aida was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new geranium are stabilized and reproduced true to type in successive generations of asexual reproduction.

The following traits have been repeatedly observed and are determined to be the unique characteristics of HWD Aida. These characteristics in combination distinguish HWD Aida as a new and distinct cultivar:

1. Semi-double dark red flowers.
2. Compact to medium plant size.
3. Distinctly zoned foliage.
4. Basal branching plant habit.

In comparison to the parent selection 85-10-2, plants of the new geranium are more compact and have darker green foliage. In comparison to the parent selection 85-4-4, plants of the new geranium have zoned foliage and plants are more vigorous.

The new geranium is similar in petal color to the patented cultivars Praeludium (U.S. Plant Pat. No. 6,716); Americana Scarlet (U.S. Plant Pat. No. 7,982); Designer Scarlet (U.S. Plant Pat. No. 8,669); and Fisgrand (U.S. Plant Pat. No. 8,760). Compared to plants of the cultivar Praeludium, plants of the new geranium are more compact and the zoning on the foliage is more pronounced. Compared to plants of the cultivar Americana Scarlet, plants of the new geranium have longer peduncles, fewer flowers per umbel, and the zoning on the foliage is more pronounced. Compared to plants of the cultivar Designer Scarlet, plants of the new geranium have zoned foliage. Compared to plants of the cultivar Fisgrand, plants of the new geranium have few flowers per umbel, darker green foliage, and green (not brown) leaf zonation.

The accompanying colored photograph illustrates the overall appearance of the new cultivar, showing the colors as true as it is reasonably possible to obtain in colored reproductions of this type. Flower color appears darker red than the actual flower color due to light reflectance. The photograph comprises a top perspective view of a typical potted plant of HWD Aida with one plant in a 10-cm container.

The cultivar HWD Aida has not been observed under all possible environmental conditions. The phenotype may vary somewhat with variations in environment such as temperature and light intensity, without, however, any varience in genotype. The following observations, measurements and comparisons describe plants grown in Rheinberg, Germany, under commercial practice in a glass-covered green house with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Botanical classification:

*Botanical.*—*Pelargonium×hortorum.*

*Commercial.*—Zonal Geranium.

*Cultivar.*—'HWD Aida'.

Parentage:

*Male parent.*—Proprietary selection 85-10-2.

*Female parent.*—Proprietary selection 85-4-4.

Propagation:

*Type cutting.*—Terminal cutting.

*Time to initiate roots.*—Summer: 27° C., 21 days; winter: 20° C., 28 days.

PLANT DESCRIPTION

General appearance: Rounded; compact to medium plant size; spreading; basal branching; moderately vigorous.

Foliage description:

*Arrangement.*—Generally alternate.

*Shape.*—Orbicular with rounded tip and cordate base.

*Size.*—Length: 6 to 8 cm. Width: 6 to 9 cm.

*Texture.*—Velvety; pubescent on upper and under surfaces.

*Margin.*—Crenate.

*Color.*—Young foliage, upper surface: 137A. Young foliage, under surface: 147B. Mature foliage, upper surface: 137A. Mature foliage, under surface: 147B. Zone, upper surface: 147B. Zone, under surface: Not obvious. Veins, upper surface: 144A. Veins, under surface: 144B. Petiole: 146C.

*Zonation.*—Width of zone: 1.5 cm. Location of zone: 0.5 to 1 cm from margin and 2 to 3 cm from petiole.

*Venation pattern.*—Palmate.
*Petiole.*—Length: 5 to 9 cm. Diameter: 2 to 3 mm.
Stem description:
*Internode length.*—1 to 1.5 cm.
*Stem color.*—146C.
*Lateral branch number.*—4 to 6.
*Lateral branch length.*—10 to 12 cm.

FLOWERING DESCRIPTION

Flowering habit: Freely flowering. Flowers arranged in umbels.
Natural flowering season: Year-round.
Flowers borne: Flower buds develop in apical leaf axils. Umbels are displayed above the foliage.
Quantity of inflorescences: Very floriferous; usually 6 to 8 open umbels and 6 to 8 developing umbels per plant at one time.
Umbels:
*Form.*—Rounded.
*Diameter.*—8 to 10 cm.
*Depth (height).*—5 to 6 cm.
Flowers:
*Form.*—Semi-double.
*Shape.*—Rounded.
*Quantity of flowers per umbel.*—23 to 25.
*Diameter.*—4 to 5 cm.
*Depth (height).*—1 to 1.5 cm.
Petals:
*Shape.*—Obovate with rounded tip.
*Arrangement.*—Rosette, overlapping.
*Quantity.*—6 to 7.
*Aspect.*—Flat.
*Size.*—Length: 2.5 cm. Width: 1.5 to 2.5 cm.
*Texture.*—Satiny, smooth.
*Margin.*—Entire.
*Color.*—When opening, upper surface: 43A. When opening, under surface: 41B. Upper surface: 40A. Under surface: 40C. Fading to, upper surface: Base of petals fade to 64D and mostly 41B/41C. Venous areas fading to 46B. Fading to, under surface: Fades only slightly near peduncle to 39C. Venous areas fading to 46B.
Petaloids:
*Shape.*—Irregular, generally obovate with rounded or clefted tip.
*Arrangement.*—Rosette, overlapping.
*Quantity.*—4 to 6.
*Size.*—Length: 1.5 to 2.5 cm. Width: 1 to 2 cm.
*Texture.*—Satiny, smooth.
*Margin.*—Generally entire.
*Color.*—When opening, upper surface: 43A. When opening, under surface: 41B. Upper surface: 40A. Under surface: 40C. Fading to, upper surface: Base of petals fade to 64D and mostly 41B/41C. Venous areas fading to 46B. Fading to, under surface: Fades only slightly near peduncle to 39C. Venous areas fading to 46B.
Peduncle (umbel stem):
*Angle.*—Erect, rigid.
*Length.*—14 to 16 cm.
*Pubescence.*—Very short and fine.
*Color.*—144A.
Pedicel (individual flower stem):
*Angle.*—Erect, rigid.
*Length.*—2.5 to 3 cm.
*Pubescence.*—Very short and fine.
*Color.*—59A, fading to 146B.
Flower bud:
*Shape.*—Long, pointed, ovoid.
*Length.*—1 to 1.5 cm.
*Diameter.*—0.75 to 1 cm.
*Color.*—44A.
Sepals:
*Arrangement.*—Rosette.
*Quantity.*—7 to 8.
*Size.*—Length: 0.5 cm. Width: 1 to 1.5 cm.
*Shape.*—Acuminate with apiculate tip.
*Texture.*—Velvety.
*Margin.*—Entire.
*Color.*—Upper surface: 39D at base fading to 45C at tip. Under surface: 55C at base fading to 45C at tip.
Reproductive organs:
*Androecium.*—Stamen number: 8 to 10. Anther size: 2 mm. Anther color: 184B. Pollen color: 171B.
*Gynoecium.*—Pistil number: 1. Pistil length: 1 cm. Stigma shape: Decurrent. Stigma color: 47C. Style length: 4 mm. Style color: 46B.
Ploidy level: Tetraploid.
Disease resistance: No fungal, bacterial nor viral problems observed.
Seed development: Seed production is very rarely observed.

It is claimed:

1. A new and distinct cultivar of geranium plant named HWD Aida, as illustrated and described.

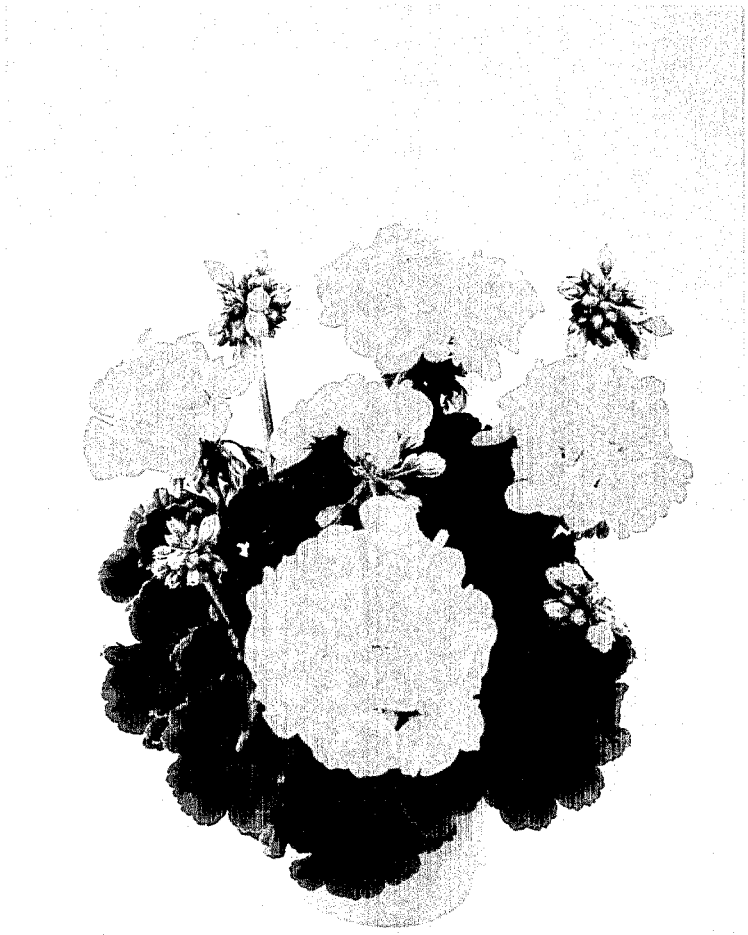

* * * * *